(12) United States Patent
Profio et al.

(10) Patent No.: US 11,000,254 B2
(45) Date of Patent: May 11, 2021

(54) METHODS AND SYSTEMS FOR PATIENT SCAN SETUP

(71) Applicant: General Electric Company, Schenectady, NY (US)

(72) Inventors: Mark Vincent Profio, Elm Grove, WI (US); Adam Pautsch, Oconomowoc, WI (US); Darin Robert Okerlund, Muskego, WI (US); Scott McOlash, Wauwatosa, WI (US); Vijay Subramanian, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 607 days.

(21) Appl. No.: 15/359,219

(22) Filed: Nov. 22, 2016

(65) Prior Publication Data

US 2018/0140270 A1    May 24, 2018

(51) Int. Cl.
*A61B 6/00*      (2006.01)
*A61B 6/03*      (2006.01)
(Continued)

(52) U.S. Cl.
CPC ............ *A61B 6/545* (2013.01); *A61B 5/0555* (2013.01); *A61B 5/704* (2013.01); *A61B 6/032* (2013.01);
(Continued)

(58) Field of Classification Search
CPC .......... A61B 6/00; A61B 6/04; A61B 6/0407; A61B 6/0457; A61B 6/0492; A61B 6/10; A61B 6/46; A61B 6/463; A61B 6/464; A61B 6/48; A61B 6/488; A61B 6/54; A61B 6/542; A61B 6/544; A61B 6/545; A61B 6/547; A61B 6/58; A61B 6/582; A61B 6/589; A61B 34/00; A61B 34/10; A61B 34/20; A61B 34/25; A62B 2034/107; A62B 2034/2046; A62B 2034/2055; A62B 2034/2057; A62B 2034/2065; A62B 2560/02; A62B 2560/0223; A62B 2560/0266; A61N 5/10; A61N 5/103;
(Continued)

(56) References Cited

U.S. PATENT DOCUMENTS 5,457,724 A     10/1995  Toth
5,870,450 A *    2/1999  Khutoryansky ..... A61B 6/4283
                                                    378/181
(Continued)

FOREIGN PATENT DOCUMENTS

KR        20140141249 A      12/2014

OTHER PUBLICATIONS

International Search Report and Written Opinion for International Application No. PCT/US2017/059042 dated Feb. 27, 2018. 14 pages.
(Continued)

*Primary Examiner* — Anastasia Midkiff (57) ABSTRACT

Methods and systems are provided for automatically adjusting a position of a table configured to be positioned in a bore of a medical imaging device. The table may be adjusted according to one or more of a table elevation, an anatomical reference, and a start scan location. The table elevation, anatomical reference, and start scan location may be obtained from a selected imaging protocol.

20 Claims, 4 Drawing Sheets

(51) Int. Cl.
*A61B 6/04* (2006.01)
*A61B 6/08* (2006.01)
*A61B 5/055* (2006.01)
*A61B 5/00* (2006.01)

(52) U.S. Cl.
CPC .......... *A61B 6/0407* (2013.01); *A61B 6/0487* (2020.08); *A61B 6/08* (2013.01); *A61B 6/4435* (2013.01); *A61B 6/467* (2013.01)

(58) Field of Classification Search
CPC .. A61N 5/1037; A61N 5/1048; A61N 5/1049; A61N 5/1064; A61N 5/1069; A61N 5/107; A61N 5/1075; A61N 2005/105; A61N 2005/1059; G01T 1/2978; G01T 7/00; G01T 7/005; G01N 2223/30; G01N 2223/302; G01N 2223/303; G01N 2223/305; G01N 2223/306; G01N 2223/32; G01N 2223/323; G06T 1/00; G06T 1/0007; G06T 1/0014; G06T 7/0012; G06T 7/0014; G06T 7/20; G06T 7/30; G06T 7/32; G06T 7/33; G06T 7/337; G06T 7/344; G06T 7/60; G06T 7/66; G06T 7/70; G06T 7/73; G06T 7/74; G06T 7/75; G06T 2207/00; G06T 2207/10; G06T 2207/10072; G06T 2207/10081; G06T 2207/10116; G06T 2207/20; G06T 2207/20228; G06T 2211/00; G06T 2211/40
See application file for complete search history.

(56) References Cited

U.S. PATENT DOCUMENTS

| | | |
|---|---|---|
| 6,195,409 B1 | 2/2001 | Chang et al. |
| 6,269,501 B1 | 8/2001 | Li et al. |
| 6,466,639 B2 | 10/2002 | Nukui et al. |
| 7,068,751 B2 | 6/2006 | Toth et al. |
| 7,623,736 B2 | 11/2009 | Viswanathan |
| 7,639,782 B2 | 12/2009 | Zelnik et al. |
| 2005/0267348 A1* | 12/2005 | Wollenweber ......... A61B 6/544 600/407 |
| 2007/0053503 A1 | 3/2007 | Zelnik et al. |
| 2009/0285357 A1 | 11/2009 | Khamene et al. |
| 2010/0002924 A1* | 1/2010 | Park ...................... A61B 6/032 382/131 |
| 2010/0232573 A1* | 9/2010 | Ozawa .................... A61B 6/04 378/95 |
| 2012/0108952 A1 | 5/2012 | Stern et al. |
| 2012/0172700 A1 | 7/2012 | Krishnan et al. |
| 2014/0123388 A1* | 5/2014 | Filiberti ............... A61N 5/1049 5/601 |
| 2014/0210468 A1 | 7/2014 | Xu |
| 2014/0355735 A1 | 12/2014 | Choi |
| 2015/0073255 A1* | 3/2015 | Liu ...................... A61B 5/0037 600/407 |
| 2016/0023019 A1* | 1/2016 | Filiberti ............... A61N 5/1075 600/1 |
| 2016/0074004 A1* | 3/2016 | Braun .................. A61B 6/0457 378/205 |
| 2016/0092078 A1 | 3/2016 | Braun et al. |

OTHER PUBLICATIONS

English Abstract of Cited Ref No. 2—KR20140141249; Espacenet Bibliographic Data; Nov. 20, 2020; 1 page.

Korean application 10-2019-7015468 filed May 29, 2019—Office Action dated Oct. 7, 2020; 6 pages.

* cited by examiner

METHODS AND SYSTEMS FOR PATIENT SCAN SETUP

FIELD

Embodiments of the subject matter disclosed herein relate to non-invasive diagnostic imaging, and more particularly, to systems and methods for automating patient setup in computed tomography (CT) imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

In modern CT systems, a gantry—a circular frame with an x-ray tube on one side and a detector on the other—rotates around a patient positioned on a table, producing several thousand sectional views of the patient in one rotation. The systems require several manual steps to be performed by a system operator to prepare the patient for scanning, including positioning and orienting the patient on the table, setting an anatomically relevant start scan location, and adjusting table elevation to properly center the patient for a desired image quality and dose performance. This setup takes time and introduces an opportunity for user error, which may affect scan reproducibility and robustness.

BRIEF DESCRIPTION

In one embodiment, a method for a medical imaging device comprises receiving a selection of an imaging protocol, determining one or more of a table elevation, an anatomical reference, and a start scan location based on the imaging protocol, and adjusting a position of a table to a determined position based on the one or more of the table elevation, the anatomical reference, and the start scan location, the table configured to be positioned in a bore of the medical imaging device. In this way, the position of the table may be automatically adjusted according to one or more parameters specified by an imaging protocol. The imaging protocol may be selected by an operator, for example, and may include a clinical intent identifier, which may specify the patient anatomy to be scanned, intent of the scanning, and/or other information defining a scanning session where imaging is performed by the medical imaging device. In doing so, the number of steps performed by the operator prior to initiation of scanning may be reduced, thus saving time during the scanning process. Further, in some examples, real-time information regarding the position of the patient may be obtained by an imaging sensor, such as a depth and/or visible light sensor, and the table position may be further adjusted according to the actual location of the patient, which may increase accuracy of positioning the patient in a desired position for scanning and may reduce patient exposure to ionizing radiation by reducing or eliminating the need for scout scans.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 4:
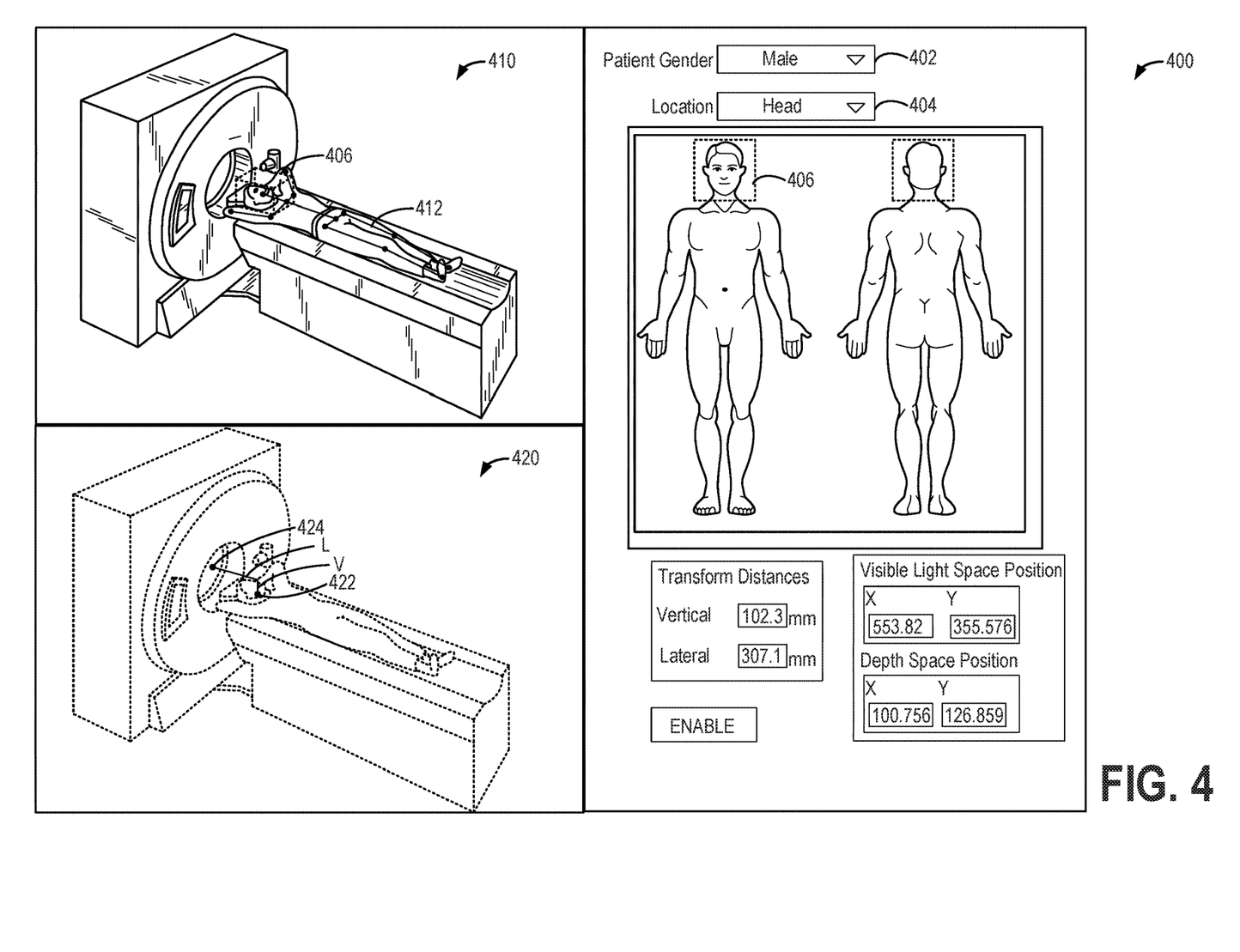
FIG. 4 is an example user interface.
Figure 5:
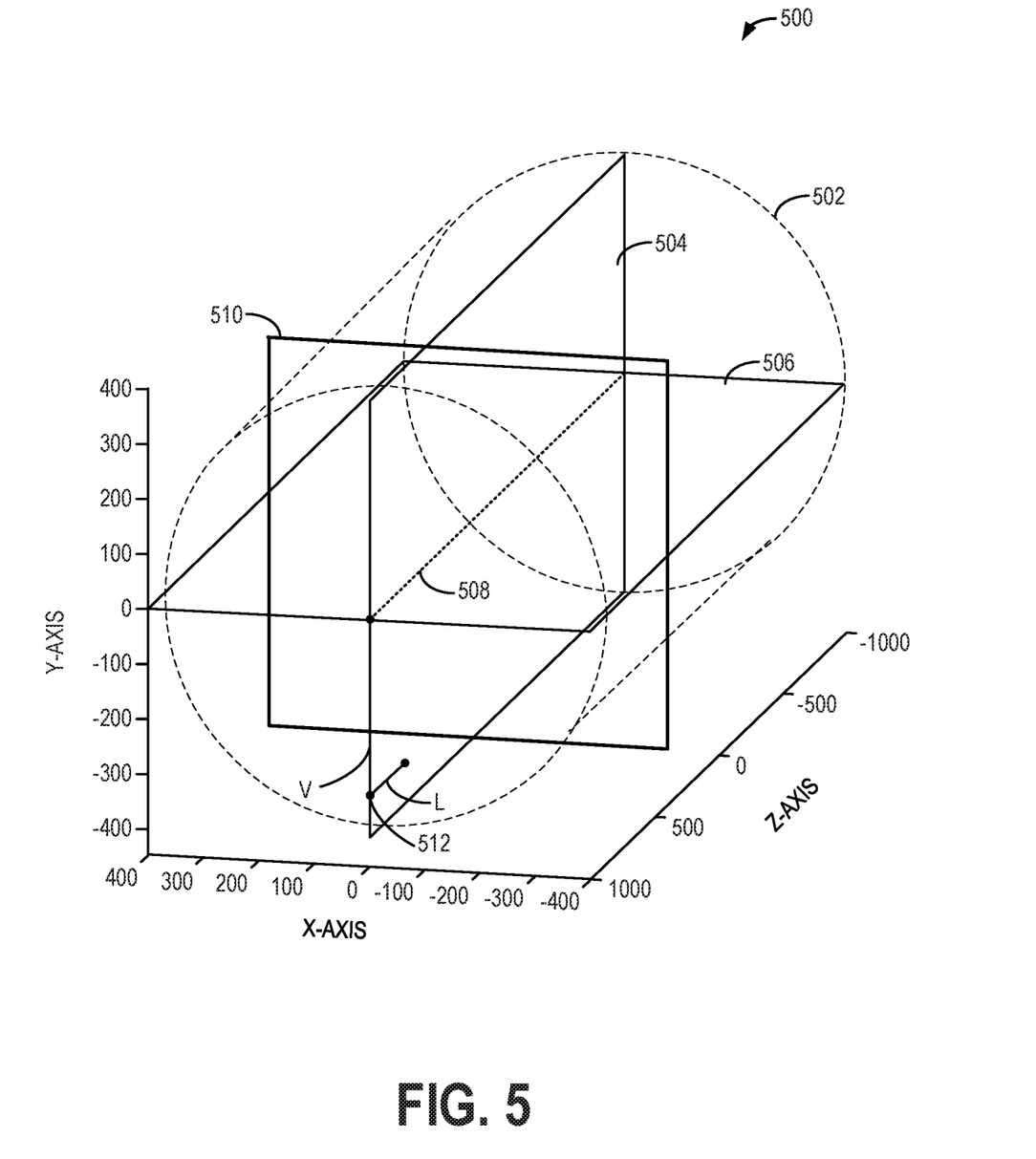
FIG. 5 is a diagram illustrating an example gantry bore and associated imaging planes.

The following description relates to various embodiments of medical imaging systems. In particular, methods and systems are provided for automated, clinical task-driven patient scan setup. An example of a computed tomography (CT) imaging system that may be used to acquire medical images in accordance with the present techniques is provided in FIGS. 1 and 2. The CT imaging system of FIGS. 1-2 includes a table positionable within a gantry of the CT imaging system, where the gantry includes an x-ray projector and detector for imaging a subject positioned on the table. The position of the table may be adjusted in order to place the subject at a desired position within the gantry for imaging. A method for automated scan setup and patient positioning, such as the method depicted in FIG. 3, may determine the table position based on a clinical intent of the exam, patient demographics (e.g., height, weight, and gender), and a 3D patient envelope (for example, as determined by a 3D scanner). The table may be adjusted according to the method of FIG. 3 in order to align the table with designated scan planes of the imaging system, as shown by FIG. 5. An example user interface that may be displayed to an operator during the execution of method 300 is illustrated in FIG. 4. An advantage that may be realized in the practice of some embodiments of the described systems and techniques is that automating patient positioning and scan setup may save time, lower the opportunity for operator error, and increase scan reproducibility.

Though a CT system is described by way of example, it should be understood that the present techniques may also be useful when applied to images acquired using other imaging modalities, such as PET, MM, image-guided systems, and so forth. The present discussion of a CT imaging modality is provided merely as an example of one suitable imaging modality.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and is generally referred to as an "imaging plane" or "scan plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all of the detectors is acquired separately to produce a transmission profile.

In third-generation CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on, for example, a cathode ray tube display.

Figure 1:
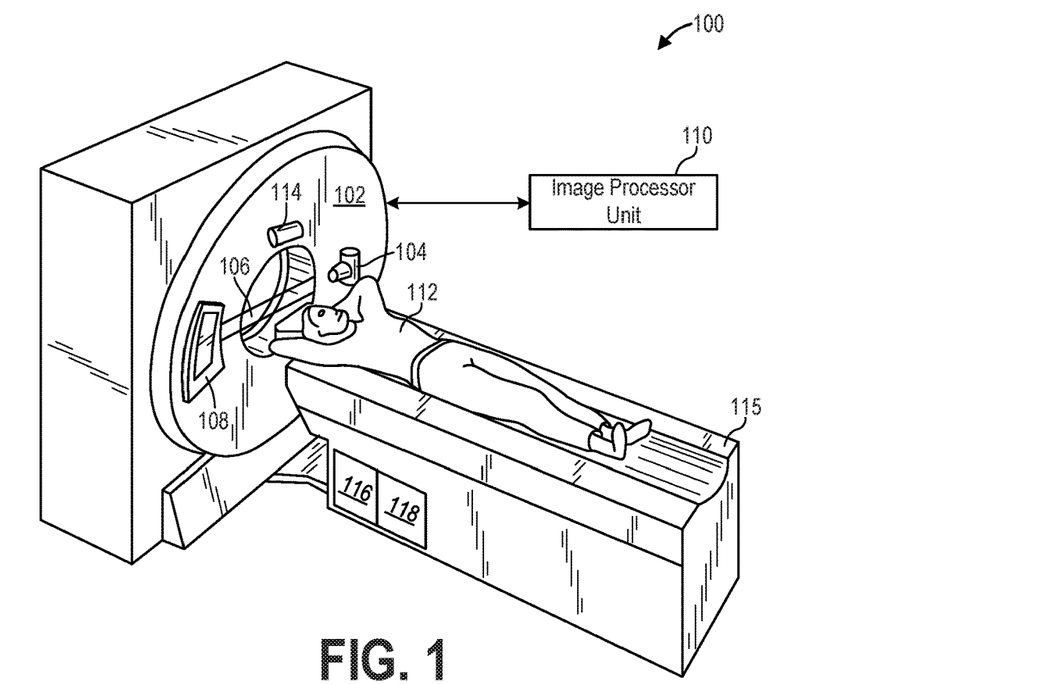
FIG. 1 shows a pictorial view of an imaging system according to an embodiment of the invention.

FIG. 1 illustrates an exemplary CT system 100. Particularly, the CT system 100 is configured to image a subject 112 such as a patient, an inanimate object, one or more manufactured parts, and/or foreign objects such as dental implants, stents, and/or contrast agents present within the body. Throughout the disclosure, the terms subject and patient may be used interchangeably, and it is to be understood that a patient is one type of subject that may be imaged by the CT system, and that a subject may include a patient, at least in some examples. In one embodiment, the CT system 100 includes a gantry 102, which in turn may further include at least one x-ray radiation source 104 configured to project a beam of x-ray radiation 106 for use in imaging the patient. Specifically, the radiation source 104 is configured to project the x-rays 106 toward a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In some examples, CT system 100 may include an imaging sensor 114 positioned on or outside the gantry 102. As shown, the imaging sensor 114 is positioned on an external side of the gantry 102 and orientated to image the subject 112 when the subject is at least partially outside the gantry 102. The imaging sensor 114 may include a visible light sensor and/or and an infrared (IR) sensor that includes an IR light source. The IR sensor may be a three-dimensional depth sensor such as a time-of-flight (TOF), stereo, or structured light depth sensor operable to generate three-dimensional depth images, while in other implementations the infrared sensor may be a two-dimensional IR sensor operable to generate two-dimensional IR images. In some implementations, a two-dimensional IR sensor may be used to infer depth from knowledge of IR reflection phenomena to estimate three-dimensional depth. Whether the IR sensor is a three-dimensional depth sensor or a two-dimensional IR sensor, the IR sensor may be configured to output a signal encoding an IR image to a suitable IR interface, which may be configured to receive the signal encoding the IR image from the IR sensor. In other examples, the imaging sensor may further include other components, such as a microphone to enable the reception and analysis of directional and/or non-directional sounds coming from an observed subject and/or other sources.

In certain embodiments, the CT system 100 further includes an image processing unit 110 configured to reconstruct images of a target volume of the patient using a suitable reconstruction method, such as an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as adaptive statistical iterative reconstruction (ASIR), conjugate gradient (CG), maximum likelihood expectation maximization (MLEM), model-based iterative reconstruction (MBIR), and so on to reconstruct images of a target volume of the patient.

CT system 100 further includes a table 115 on which a subject to be imaged may be positioned. The table 115 may be motorized so that the vertical and/or lateral position of the table may be adjusted. Accordingly, table 115 may include a motor 116 and a motor controller 118. The table motor controller 118 moves the table 115 by adjusting the motor 116 for appropriately positioning the subject in the gantry 102 for acquiring projection data corresponding to the target volume of the subject. Table motor controller 118 may adjust both the elevation of table 115 (e.g., the vertical position relative to a ground on which the table sits) and lateral position of table 115 (e.g., the horizontal position of the table along an axis parallel to a rotational axis of the gantry).

Figure 2:
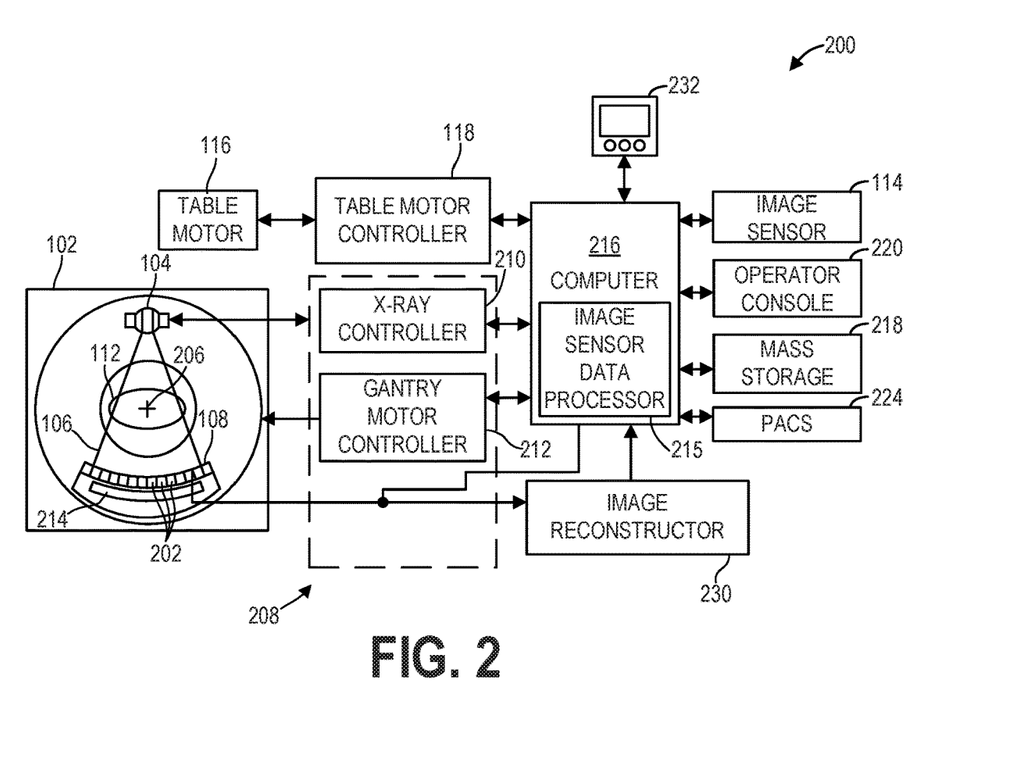
FIG. 2 shows a block schematic diagram of an exemplary imaging system according to an embodiment of the invention.

FIG. 2 illustrates an exemplary imaging system 200 similar to the CT system 100 of FIG. 1. In one embodiment, the system 200 includes the detector array 108 (see FIG. 1). The detector array 108 further includes a plurality of detector elements 202 that together collect the x-ray beams 106 (see FIG. 1) that pass through the subject 112 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 112 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 112 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

As described further herein, the computing device 216 uses the operator-supplied and/or system-defined commands and parameters to operate the table motor controller 118, which in turn, may control the motorized table 115. For example, the computing device 216 may send commands to the motor controller 118 instructing the motor controller 118 to adjust the vertical and/or lateral position of the table 115 via the motor 116.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230. In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

As described further herein, the computing device 216 may include computer-readable instructions executable to send commands and/or control parameters to one or more of the DAS 214, the x-ray controller 210, the gantry motor controller 212, and the table motor controller 226 according to an exam imaging protocol that includes clinical task/intent, also referred to herein a clinical intent identifier (CID) of the exam. For example, the CID may inform on the goal of the procedure (e.g., general scanning or lesion detection, anatomy of interest, critical to quality (CTQ) parameters, or other goals) based on a clinical indication, and may further define the desired subject position and orientation during the scanning (e.g., supine and feet first). The operator of the system 200 may then position the subject on the table according to subject position and orientation specified by the imaging protocol. Further, the computing device 216 may set and/or adjust various scan parameters (e.g., dose, angle of gantry rotation, kV, mA, attenuation filters) according to the imaging protocol. The imaging protocol may be selected by the operator from among a plurality of imaging protocols stored in memory on the computing device 216 and/or a remote computing device, or the imaging protocol may be selected automatically by the computing device 216 according to received patient information, for example.

During an exam/scanning session, it may be desirable to expose the subject to as low a dose of radiation as possible while still maintaining desired image quality. Additionally, reproducible and consistent imaging quality may be desired from exam to exam and subject to subject, and across different imaging system operators. As such, the imaging system operator may perform manual adjustments to the table position to center a desired patient anatomy in the center of the bore of the gantry, for example. However, such manual adjustments may be prone to error and/or may take a relatively long amount of time. Therefore, the CID associated with the selected imaging protocol may be mapped to various subject positioning parameters, including table elevation, an anatomical reference for the scanning, and a start and/or end scan location. Based on these subject positioning parameters, and further based on information about the subject (such as height, weight, gender, and age), the table position may be automatically adjusted in order to position in the subject in a desired position for scanning. By automatically positioning the subject according to the CID, operator errors in subject positioning may be reduced, thus reducing the likelihood the subject will be exposed to higher-than-desired radiation dose and increasing the quality and reproducibility of the images generated from the scanning. Further, the amount of time the imaging system operator spends positioning the subject may be reduced, allowing for more scans to be performed in a day and/or allowing for additional subject interaction.

Accordingly, the computing device 216 may include instructions for automatically adjusting the table position within the gantry bore, including the table elevation and lateral position, based on the CID of the selected imaging protocol. For example, a look-up table stored in memory of computing device 216 may map the selected CID to a table elevation, subject anatomical reference, and start scan location. The table elevation may correspond to an anatomical reference plane (e.g., mid-coronal plane), and the lateral position may correspond to a patient anatomical reference (e.g., iliac crest) and a start scan location (e.g., a distance offset from the anatomical reference, whether superior or inferior). The position of the table may be further adjusted based on patient information/demographics (e.g., patient gender, height, and weight) and/or 2D or 3D patient envelope imagery, as described below.

Additionally, in some examples, computing device 216 may include an image sensor data processor 215 that includes instructions for processing imaging information received from an imaging sensor, such as sensor 114 of FIG. 1. The information received from the imaging sensor, which may include depth information and/or visible light information, may be processed to determine various subject parameters, such as subject identity, subject size (e.g., height, weight, patient envelope), and current subject position relative to the table and the imaging sensor. These subject parameters may be used by the computing device 216, for example, to adjust the position of the table, as will be described in more detail below. Further, video stream(s) from the imaging sensor may be displayed via display 232.

The information from the image sensor may be usable by the image sensor data processor 215 to perform tracking of one or more subjects in the field of view of the image sensor. In one example, the image information (e.g., depth information) may be used to perform skeletal tracking, wherein a plurality of joints of the subject are identified and analyzed to determine movement, pose, position, etc., of the subject. The location of the joints during skeletal tracking may be used to determine the subject parameters described above.

Figure 3:
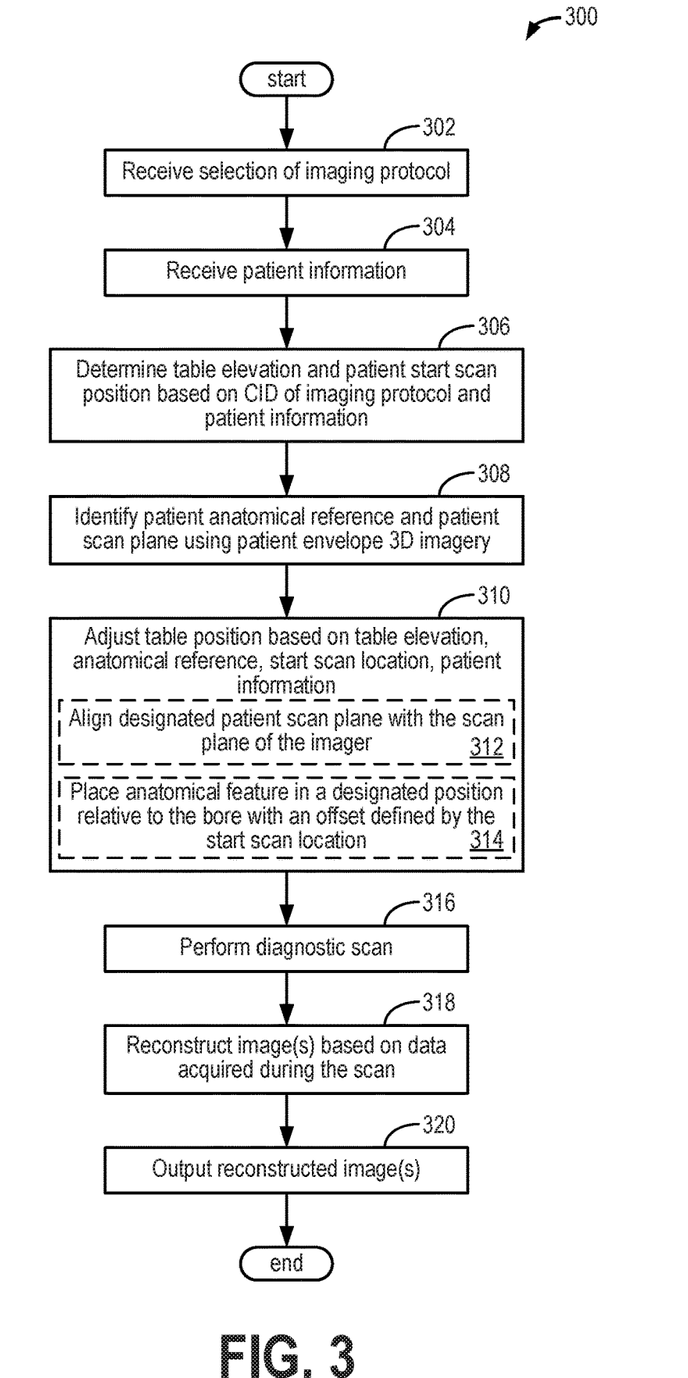
FIG. 3 is a flow chart illustrating an example method for automated patient scan setup and patient positioning.

FIG. 3 shows a high-level flow chart illustrating an example method 300 for automatic patient positioning and scan setup. Method 300 will be described with regard to the systems and components of FIGS. 1-2; however, it should be understood that the method may be implemented with other systems and components without departing from the scope of the present disclosure. Method 300 may be carried out according to executable instructions stored in non-transitory memory on a computing device, such as computing device 216 of FIG. 2.

Method 300 begins at 302 and includes receiving a selection of an imaging protocol including an associated CID. An operator of the imaging system may select, via a user interface of the imaging system, an imaging protocol that specifies the anatomy and clinical intent of the exam. The imaging protocol includes a CID that defines the objective of the scan. For example, the CID may comprise an indication of a task (such as detection, screening, and so on) and corresponding patient orientation for the exam (e.g., supine or prone, head-first or feet-first). The CID may further comprise an indication of a targeted contrast level, a targeted lesion size, CTQs, and so on. For example, a first CID may include CTQs that indicate spatial resolution is to be prioritized, while a second CID may include CTQs that indicate image quality is to be prioritized. For some screening tasks, for example, a corresponding CID may include CTQs that indicate dose is important. Other CTQs that may be prioritized include x-ray dose target, temporal resolution, contrast to noise ratio, signal to noise ratio, and low contrast detectability. Further, the CID may include instructions displayed to the exam operator (such as via display 232 of FIG. 2) regarding patient positioning. For example, if a stroke is indicated, a neuro CID may be selected that includes instructions for the exam operator to orient the patient head-first and supine on the table.

As used herein, CID defines a flag or cue to the system of a desired clinical intent. It is independent of the scanning protocol and the protocol name (which may be operator-defined and therefore may not be identifiable as a system cue). In other words, while each scanning protocol may include an associated CID, more than one scanning protocol may include a given CID and any scan session parameters defined by the scanning protocols that are not defined by the CID are not germane nor necessarily identifiable by the system in order to execute the table adjustments defined herein. The CID informs the system and provides an opportunity for specific customizations appropriate for the clinical intent. In particular, the CID builds a system-wide reference protocol for a patient average size and shape and provides the opportunity to cover a wider dynamic range of patient sizes and shapes with one overall meta-protocol.

At 304, the method includes receiving patient information. For example, patient information may be input by the scan operator or may be obtained from an electronic health/medical record. Patient information may include, but is not limited to, patient gender, patient size (e.g., height and weight), previous exposure history, and so on. Previous exposure history of the patient may be taken into account when determining radiation dose level. For example, the previous exposure history may provide constraints (e.g., an upper limit) on the dose level such that patients with large amounts of previous radiation exposure may be presently exposed to lower dose levels than patients with small amounts of previous radiation exposure. Previous exposure history may also be used as a reference to guide the appropriate dose target selection for the patient under study. Furthermore, patient information, such as patient gender, may be used to restrict the scan area as to avoid scanning reproductive organs if permitted.

Additionally or alternatively, the patient information may be obtained at least partially from imaging information obtained by an imaging sensor, such as imaging sensor 114. For example, prior to and/or after being positioned on the table, imaging information of the patient may be collected in order to perform skeletal tracking, perform facial recognition, determine patient size, and/or perform other actions. Facial recognition may be performed to confirm the identity of the patient, for example, if the patient has been scanned previously. Performing facial recognition may help ensure that the correct electronic health record is associated with the patient, for example. Further, in some examples, the imaging information may continue to be collected once the patient is positioned on the table, in order to ascertain a current position of the patient on the table relative to the gantry, identify an anatomical feature of interest, and/or other patient information.

At 306, the method includes determining the table elevation and patient start scan position based on the selected CID and patient information. For example, the method may reference a lookup table mapping the CID to a table elevation, anatomical reference, and start scan position (e.g., lateral table position) for an expected/average patient size in order to coarsely position the table. In the example of the neuro CID, the table elevation may define a position in which the mid-coronal plane of the patient is expected to be centered in the gantry bore, and the start scan location may define a lateral position of the table to center the expected location of the anatomical reference (e.g., orbital meatal line) of the patient at a position defined by the start scan location (e.g., the orbital meatal line may be positioned 22.5 mm inferior to the scan plane of the x-ray projector). The table elevation and start scan location may be refined based on the patient information (as input by the scan operator, as obtained from the electronic health record, and/or as determined from the depth and/or visible light imaging information). For example, a taller patient may require a different lateral table position than a shorter patient to center the same anatomical reference (e.g., the orbital meatal line) within the scan plane of the imaging source.

At 308, method 300 optionally includes identifying the patient anatomical reference and patient scan plane using patient envelope 3D imagery. That is, depth and/or visible light information acquired by the imaging sensor may be used to define the patient envelope (e.g., the surface area and volume of the patient), which in turn may be used to determine the position of the patient (or anatomical feature) relative to the imaging source. Further, skeletal tracking may be used to identify a joint nearest the anatomical reference as a proxy for identifying the actual anatomical reference on the patient. Additionally or alternatively, a scout scan using the x-ray projector and detector may be performed for further positioning precision. However, performing a scout scan may increase the overall radiation dose compared with using patient envelope 3D imagery alone. If more than one scan is performed during an imaging session (e.g., more than one CID is associated with the imaging protocol, or more than one imaging protocol is selected), the patient envelope may be redefined with new data acquired by the imaging sensor. Alternatively, data from the previous scan may be used.

At 310, the method includes adjusting the table position based on the table elevation, anatomical reference, start scan location, and patient information. In one example, the table position may be adjusted by the table motor controller 226, and the computing device 216 may send commands to the table motor controller to adjust the position of the table.

As described above, the table elevation may represent a designated scan plane of the subject, such as a mid-coronal plane, rather than an absolute table height. The designated scan plane of the subject may be translated into a table height based on the size of the subject, dose parameters, and/or other CTQs that define where the desired scan plane is to be positioned within the bore. For example, a plane of the gantry bore (or a plane of the imager/x-ray projector) where the designated scan plane of the patient is to be positioned may be determined based on the dose parameters or other CTQs (e.g., the dose parameters or other CTQs may indicate the designated scan plane is to be aligned with the coronal central plane of the bore). In one example, a target distance between a centroid of the patient (e.g., center of mass) and the imager/x-ray projector may be defined by the dose parameters or other CTQs and the table elevation may be adjusted so that the designated scan plane of the patient is at the target distance. Further, the table height that will position the designated scan plane of the subject at the designated plane of the gantry may be identified in the CID look-up table according to an average patient height and weight. Then, the known patient information may be used to further adjust the table height so that the patient's actual designated scan plane aligns with the plane of the gantry bore. The adjustment of the table elevation may include aligning the designated patient scan plane with the scan plane of the imager and/or gantry bore, as indicated at 312. In a further example, patient depth and/or visible light information may be used to adjust the table elevation to align the designated patient scan plane within the scan plane of the imaging source. For example, a distance between a centroid or joint of the patient (e.g., a hip center joint identified via skeletal tracking) and the plane of interest of the gantry bore may be determined and the table elevation may be adjusted until the centroid aligns with the plane of interest.

An example gantry bore and associated planes are illustrated in FIG. 5. A diagram 500 of FIG. 5 includes a gantry bore 502, sagittal center plane 504, and coronal center plane 506 plotted along a set of axes (x, y, and z). The sagittal center plane 504 and coronal center plane 506 intersect along a rotational axis 508 of the gantry. The sagittal center plane 504 extends along the y-axis and z-axis and is aligned with the zero coordinate of the x-axis. The coronal center plane 506 extends along the x-axis and z-axis and is aligned with the zero coordinate of the y-axis. Further, a z-axis scan plane, which may define the start scan location, for example, is shown by scan plane 510, which extends along the y-axis and x-axis and is aligned with the zero coordinate of the z-axis. An anatomical reference of the subject, such as a centroid of the subject's head, is shown at location 512. As such, in the example presented above with respect to FIG. 3, the table elevation (shown by vertical height V) may be adjusted along the y-axis of FIG. 5, for example, such that the designated scan plane (e.g., the mid-coronal plane) of the subject is aligned with the coronal center plane of the gantry bore.

The anatomical reference and start scan location may include an anatomical feature of the patient (such as a sternal notch, iliac crest, or orbital meatal line) and a distance offset from the anatomical feature at which scanning is to begin. Thus, based on the anatomical reference and start scan location and further based on an average patient size, the table lateral position may be adjusted so that an expected location of the anatomical feature corresponding to the reference is positioned relative to the x-ray projector at the offset defined by the start scan location. This lateral table position may then be further adjusted according to the patient's actual height and/or weight, for example. Accordingly, adjusting the table position may further include placing the patient anatomical feature in a designated position relative to the bore with an offset defined by the start scan location, as indicated at 314. In the example of the neuro CID, the start scan location may be offset a distance (e.g., 22.5 millimeters) inferior to the orbital meatal line of the patient. In a further example, patient depth and/or visible light information may be used to adjust the lateral table position to place the anatomical feature of the patient at the specified location. For example, the position of the orbital meatal line of the patient may be approximated by the head joint identified during skeletal tracking, and thus the distance between the head joint of the patient and the scan plane of the imager may be determined and the lateral table position may be adjusted until the head joint is positioned at the offset defined by the start scan location (e.g., 22.5 mm inferior). In other examples, feature recognition may be performed with the visible light and/or depth information to identify the actual location of the orbital meatal line of the patient.

Referring again to the example gantry bore illustrated in FIG. 5, the scan plane 510 of the x-ray projector may extend along the x-axis and may be aligned with the zero coordinate values of the z-axis. The table may be adjusted laterally (along the z-axis) with a lateral distance L in order to position the anatomical feature of the subject (e.g., the centroid of the subject's head) at the position specified by the start scan location (e.g., 22.5 mm inferior to the scan plane of the x-ray projector).

At 316, the method includes performing the diagnostic scan. The diagnostic scan may be initiated by the scan operator by inputting a start command at the operator console (such as operator console 220 of FIG. 2). Alternatively, the diagnostic scan may be automatically initiated responsive to the table reaching the desired scanning position. During the diagnostic scan, the imaging source (e.g., x-ray projector) is activated according to the parameters specified by the imaging protocol (e.g., at a specified kV, mA, attenuation filter position) and the rotation of the gantry is controlled to achieve the scan angles specified by the imaging protocol. Further, during the scan, the position of the table may be moved such that the scan progresses from the start scan location to the stop scan location.

At 318, the method includes reconstructing the image(s) based on data acquired during the scan. The one or more images may be reconstructed using, as a non-limiting example, an analytic reconstruction algorithm, such as filtered backprojection or an iterative reconstruction algorithm. At 320, the method includes outputting the reconstructed image(s). For example, the one or more images may be output to a display device, such as display 232 of FIG. 2. In this way, the operator of the imaging system may review the image(s). Method 300 then ends.

In this way, patient positioning may be automated, decreasing setup time and the opportunity for operator error. By using the 3D patient envelope, table elevation accuracy may be improved, which may in turn improve the quality of the resulting images. Further, automating the scan setup process may allow the operator to focus more on patient care.

In the method described above, imaging information (e.g., visible light and/or depth information) may be used to confirm patient identity as well as automatically adjust the position of the table. In some examples, additionally or alternatively, the imaging information may be displayed to the operator of the imaging system. An example user interface 400 that may be displayed on a display device during patient set up prior to scanning is illustrated in FIG. 4. The user interface 400 may include a visible light image 410 captured by an imaging sensor (such as sensor 114 of FIG. 1) and a depth image 420 captured by the imaging sensor. It is to be understood that depth image 420 is exemplary in nature and is presented to illustrate a differential appearance from the visible light image. The appearance of depth image 420 is not limiting and may take other forms without departing from the scope of the disclosure. Further, while imaging sensor 114 of FIG. 1 was shown as being positioned on the gantry, it is to be understood that the sensor could be positioned at a different location in order to capture the perspective shown in FIG. 4, and that other perspectives of the subject, table, and gantry are within the scope of the this disclosure.

The user interface 400 also presents data from the imaging sensor in response to input from the operator, for example. The user interface may include a first drop down menu 402 that allows the operator to specify patient gender and a second drop down menu 404 that allows the operator to specify a region of interest (location). The drop-down menu allowing selection of patient gender is exemplary and other mechanisms for identifying patient gender, age, height, weight, BMI, medical allergies and so on may be possible, such as from an electronic medical record or from depth and/or visible light imagery. Further, the patient gender and region of interest may be initially specified by the scanning protocol/CID. For example, the region of interest could be automatically adjusted and placed by the combination of the CID, patient information, and visible imagery system inputs. Herein, the operator has selected a male patient gender and a head region of interest. A preview image is illustrated showing the defined region of interest 406 relative to an example patient. In one example, the operator may move the region of interest 406 by performing a drag operation on the display device or by performing an alternate user input.

Various information relating to the region of interest may be displayed via user interface 400. For example, visible light space and depth space positions of the imaged subject corresponding to a centroid of the region of interest are shown. For example, the centroid of the head may be positioned at the illustrated visible light and depth x,y coordinates. The visible light space position and depth space position may include raw image information sent from the image sensor. These coordinates may be mathematically transferred to the coordinate system of the imaging system (e.g., the x, y, and z axes of the gantry bore, as shown in FIG. 5).

As shown in FIG. 4, the selected region of interest 406 is schematically shown in the visible light image 410. Further, as explained previously, the visible light and/or depth image information may be used to perform skeletal tracking, and an example skeleton 412 of the subject including a plurality of joints is also shown in visible light image 410. It is to be understood that the illustrated region of interest and skeleton are exemplary and may take on different forms, and further that the region of interest and skeleton are presented for illustrative purposes may not actually be illustrated on user interface 400.

The operator may command further table adjustments based on the information presented in user interface 400. For example, the operator may command the table elevation be adjusted until the depth measurement of the centroid of the head is aligned with the scan plane of the imager. In some examples, the computing device of the imaging system (e.g., device 216) may obtain the information displayed via user interface 400 and use the information to automatically adjust the table position. For example, as explained above, the visible light and depth space positions may be transferred to the coordinates of the imaging system, and a vertical and/or lateral table adjustment may be performed to position the table and hence subject at the designated position. As shown by depth image 420, a head joint 422 of the subject (which may correspond to the centroid of the subject's head) may be identified and a vertical transformed distance V and a lateral transformed distance L identified in order to move the head joint 422 to a start scan location 424, for example.

Further, in some examples, the depth and/or visible light information may be used to perform rationality or consistency checks on the scanning session. For example, based on the depth and/or visible light information, the imaging system computing device may determine that the patient is positioned too close to the x-ray projector and may output a notification to the operator (e.g., a displayed notification of the patient position). In another example, based on the depth and/or visible light information, the computing device may determine that the patient anatomy of interest is not positioned in the bore (e.g., the patient may have moved out of position) and the device may output a notification to the operator.

Thus, according to the systems and methods described herein, a medical imaging device, such as a CT system, may obtain a clinical task/intent (CID) and a protocol chosen by an operator, which inform a CT exam both of the intended size/weight/shape of the patient population (demographic) and the goals/outcomes for the procedure. User-defined (or system-defined) mapping of the CID to an anatomically relevant start scan location and a gantry centered desired table elevation in combination with optional three dimensional patient envelope imagery provides an automatic setting of the scan start location, positioned at, for example, the mid-coronal plane of the patient in the gantry bore for designated image quality and dose performance. This saves time, lowers opportunity for user error, and improves repeatability/robustness of patient scans.

To achieve the above, knowledge of a clinical context/task and associated CTQs of a scanning session/exam, which embodies the goals and outcomes for the CT exam, may be obtained. A user definition of the range of patients or demographic profile (height—size/weight/shape) anticipated for the protocol design may also be obtained. A user may create start scan locations/anatomical references and table elevation pairs profile (e.g., in a lookup table) mapping to the appropriate CID (clinical context). A computing device of the medical imaging device may include instructions for integrating clinical context and patient characteristics providing an easy method to determine and set, with user initiation, a start scan location and table elevation. Optional 3D patient envelope imagery or scout scans may be used to locate the desired anatomical reference and associated mid-coronal plane to center the patient in the gantry bore at the specified start scan location.

The technical effect of automatically adjusting a table position of a table configured to be positioned in a bore of an imaging system is to reduce operator error associated with proper patient positioning and expedite the scanning procedure.

An example provides a method for a medical imaging device comprising receiving a selection of an imaging protocol; determining one or more of a table elevation, an anatomical reference, and a start scan location based on the imaging protocol; and adjusting a position of a table to a determined position based on the one or more of the table elevation, the anatomical reference, and the start scan location, the table configured to be positioned in a bore of the medical imaging device. The method may further comprise acquiring medical imaging data with the medical imaging device responsive to the table reaching the determined position. In an example, the imaging protocol includes a clinical intent identifier and determining one or more of the table elevation, the anatomical reference, and the start scan location based on the imaging protocol comprises determining one or more of the table elevation, the anatomical reference, and the start scan location based on the clinical intent identifier. Further, adjusting the position of the table to the determined position based on the one or more of the table elevation, the anatomical reference, and the start scan location further comprises adjusting the position of the table to the determined position based on the one or more of the table elevation, the anatomical reference, and the start scan location, and further based on received patient information.

The method may further comprise receiving the patient information from one or more of operator input and an electronic medical record, and the patient information may comprise one or more of patient gender, patient age, patient height, and patient weight. In an example, the method may further comprise receiving one or more of depth information and visible light information from an image sensor and obtaining the patient information from the one or more of the depth information and visible light information. The patient information may comprise one or more of patient height, patient weight, patient gender, patient age, and patient location parameters relative to the table and relative to the bore of the medical imaging device.

The table elevation defines a designated scan plane of a patient positioned on the table, and adjusting the position of the table to the determined position based on the one or more of the table elevation, the anatomical reference, and the start scan location, and further based on received patient information may comprise determining a current location of the designated scan plane of the patient based on the patient information; and adjusting the position of the table to align the designated scan plane with a scan plane of the medical imaging device.

In examples, adjusting the position of the table to the determined position based on the one or more of the table elevation, the anatomical reference, and the start scan location, and further based on received patient information comprises identifying an anatomical feature of a patient positioned on the table that corresponds to the anatomical reference based on the patient information; and adjusting the position of the table to place the anatomical feature of the patient in a designated position relative to the bore of the medical imaging device.

The start scan location may define an offset between the anatomical reference and an imaging source of the medical imaging device, and adjusting the position of the table to place the anatomical feature of the patient in the designated position may comprise adjusting the position of the table to place the anatomical feature of the patient at the offset defined by the start scan location.

An example system comprises a rotatable gantry having a bore centrally disposed therein; a table movable within the bore and configured to position a subject for image data acquisition within the bore; an imaging source positioned within the rotatable gantry and configured to project energy toward the subject; a detector array disposed within the rotatable gantry and configured to receive energy projected by the imaging source and impinged by the subject; and a controller. The controller may be configured to receive a selection of an imaging protocol including a clinical intent identifier; determine a table elevation, an anatomical reference, and a start scan location based on the clinical intent identifier; adjust a position of the table to a scanning position based on the table elevation, the anatomical reference, and the start scan location; and acquire medical imaging data via the detector array by activating the imaging source responsive to the table being in the scanning position. In one example, the imaging source may be configured to project x-ray energy toward the subject and the detector array may be configured to receive x-rays projected by the imaging source and impinged by the subject.

The system may further comprise an imaging sensor positioned outside the bore and configured to collect one or more of depth information and visible light information. The table elevation may define a designated scan plane of the subject, the anatomical reference may define an anatomical feature of the subject, and the start scan location may define a position of the anatomical reference relative to the imaging source. To adjust the position of the table to the scanning position, the controller may be configured to determine a current position of the designated scan plane of the subject based on the one or more of the depth and visible light information and adjust an elevation of the table to align the designated scan plane of the subject with a scan plane of the imaging source. To adjust the position of the table to the scanning position, the controller may be configured to identify the anatomical feature of the subject that corresponds to the anatomical reference based on the one or more of the depth and visible light information and adjust a lateral position of the table to place the anatomical feature at the start scan location.

The system may further comprise a display device operably coupled to the controller, and the controller may be configured to send the one or more of the depth information and the visible light information to the display device. The controller may be further configured to determine one or more imaging session scan parameters from the imaging protocol, and further adjust the position of the table based on the one or more imaging session scan parameters. The one or more imaging session scan parameters may comprise one or more of a radiation dose threshold and a designated image quality.

Another example of a method for a medical imaging device includes, responsive to a selected clinical intent identifier, automatically prepositioning a table according to imaging information received from an imaging sensor, the table configured to be positioned in a bore of the medical imaging device. In an example, automatically prepositioning the table according to imaging information received from the imaging sensor comprises automatically prepositioning the table according to one or more depth information and visible light information received from the imaging sensor. The method may further comprise, after automatically prepositioning the table, acquiring medical imaging data with an image source of the medical imaging device responsive to the table reaching the determined position. The imaging sensor may be positioned outside and separate from the medical imaging device and may be communicatively coupled to the medical imaging device. The method may further comprise determining a target table elevation, reference anatomy, and target start scan location from the selected clinical intent identifier. For example, an operator of the medical imaging device may enter a user input selecting an imaging protocol that includes the clinical intent identifier, and the medical imaging device may obtain the target table elevation, reference anatomy, and target start scan location from the imaging protocol. The medical imaging device, which may include a computing device, may adjust (via the computing device and a motor of the table) a position of the table in order to position a subject on the table at the target table elevation and position an anatomical feature of the subject (that corresponds to the anatomical reference) at the start scan location, or at a designated location relative to the start scan location. The computing device may adjust the table according to feedback from the imaging information received from the imaging sensor.

Another example of a system includes a rotatable gantry having a bore centrally disposed therein; a table movable within the bore and configured to position a subject for image data acquisition within the bore; an x-ray source positioned within the rotatable gantry and configured to project a beam of x-rays toward the subject; a detector array disposed within the rotatable gantry and configured to receive x-rays projected by the imaging source and attenuated by the subject; an image sensor positioned outside the bore and configured to acquire one or more of depth information and visible light information; and a controller configured to: receive a selection of an imaging protocol; determine, from the a clinical intent identifier of the imaging protocol, a table elevation defining a designated scan plane of the subject, an anatomical reference defining an anatomical feature of the subject, and a start scan location defining a position of the anatomical reference relative to the x-ray source when scanning begins; determine one or more of a subject size, a subject location, and a location of the anatomical feature of the subject based on the one or more of the depth information and visible light information; adjust an elevation of the table based on the table elevation, subject size, and subject location; adjust a lateral position of the table based on the location of the anatomical feature of the subject and the start scan location; and perform, with the x-ray source and the detector, a scan of the object when the table is at the adjusted elevation and adjusted lateral position.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for operating a medical imaging device, comprising:
   receiving a selection of an imaging protocol including a clinical intent identifier for an imaging scan of a patient with the medical imaging device;
   determining, from the clinical intent identifier and independent of patient information, an initial table elevation and an initial lateral table position of a table configured to be positioned in a bore of the medical imaging device, where the initial table elevation defines a table height of the table that aligns a designated patient scan plane of a reference patient with a first designated scan plane of the medical imaging device and the initial lateral table position defines a table position of the table that positions a designated anatomical reference of the reference patient at a designated offset from a second designated scan plane of the medical imaging device;

adjusting one or more of the initial table elevation and the initial lateral table position based on the patient information to generate a final table elevation and a final lateral table position; and automatically adjusting the table to the final table elevation and the final lateral table position.

2. The method of claim 1, further comprising acquiring medical imaging data with the medical imaging device responsive to the table reaching the final table elevation and the final lateral table position, and wherein the clinical intent identifier is stored in memory of a computing device and is mapped, via a look-up table stored in the memory of the computing device, to the initial table elevation and the initial lateral table position.

3. The method of claim 1, further comprising receiving the patient information from one or more of operator input to a user interface and an electronic medical record.

4. The method of claim 3, wherein the patient information comprises one or more of patient gender, patient age, patient height, and patient weight, and wherein adjusting one or more of the initial table elevation and the initial lateral table position based on the patient information to generate the final table elevation and the final lateral table position further comprises adjusting the initial table elevation based on the patient information and based an x-ray dose threshold for the patient to generate the final table elevation.

5. The method of claim 1, further comprising receiving one or more of depth information and visible light information from an image sensor and obtaining the patient information from the one or more of the depth information and the visible light information.

6. The method of claim 5, wherein the patient information comprises one or more of patient height, patient weight, patient gender, patient age, and patient location parameters relative to the table and relative to the bore of the medical imaging device.

7. The method of claim 1, wherein adjusting one or more of the initial table elevation and the initial lateral table position based on the patient information to generate the final table elevation and the final lateral table position comprises:

identifying an anatomical feature of the patient positioned on the table that corresponds to the anatomical reference based on the patient information; and adjusting the initial lateral table position to place the anatomical feature of the patient at the designated offset from the second designated scan plane of the medical imaging device.

8. The method of claim 7, wherein adjusting one or more of the initial table elevation and the initial lateral table position based on the patient information to generate the final table elevation and the final lateral table position comprises:

identifying a current location of a designated patient scan plane of the patient based on the patient information; and adjusting the initial table elevation to align the designated patient scan plane of the patient with the first designated scan plane of the medical imaging device.

9. A system, comprising:
a rotatable gantry having a bore centrally disposed therein;
a table movable within the bore and configured to position a subject for image data acquisition within the bore;
an imaging source positioned within the rotatable gantry and configured to project radiation toward the subject;
a detector array disposed within the rotatable gantry and configured to receive radiation projected by the imaging source and attenuated by the subject; and
a controller configured to:
receive a selection of an imaging protocol including a clinical intent identifier;
enter the clinical intent identifier into a look-up table stored in memory of the controller;
receive, as output from the look-up table, a table elevation, an anatomical reference, and a start scan location, wherein the table elevation is determined as a function of the clinical intent identifier;
adjust a position of the table to a scanning position based on the table elevation, the anatomical reference, and the start scan location; and
acquire medical imaging data via the detector array by activating the imaging source responsive to the table being in the scanning position.

10. The system of claim 9, wherein the clinical intent identifier is the only input from the imaging protocol that is entered into the look-up table, and further comprising an imaging sensor positioned outside the bore and configured to collect one or more of depth information and visible light information.

11. The system of claim 10, wherein the table elevation defines a designated scan plane of the subject, the anatomical reference defines an anatomical feature of the subject, and the start scan location defines a position of the anatomical reference relative to the imaging source.

12. The system of claim 11, wherein to adjust the position of the table to the scanning position, the controller is configured to transform the designated scan plane into a target table height based on a size of the subject and one or more scan parameters defined by the clinical intent identifier, determine a current position of the designated scan plane of the subject based on the one or more of the depth information and the visible light information, and adjust an elevation of the table to the target table height to align the designated scan plane of the subject with a scan plane of the imaging source.

13. The system of claim 11, wherein to adjust the position of the table to the scanning position, the controller is configured to identify the anatomical feature of the subject that corresponds to the anatomical reference based on the one or more of the depth information and the visible light information, and adjust a lateral position of the table to place the anatomical feature of the subject at the start scan location.

14. The system of claim 12, wherein the one or more scan parameters defined by the clinical intent identifier include a radiation dose parameter, wherein the system further comprises a display device operably coupled to the controller, and wherein the controller is configured to send the one or more of the depth information and the visible light information to the display device.

15. A method for operating a medical imaging device, comprising:
responsive to a selected clinical intent identifier, automatically prepositioning a table as a function of the selected clinical intent identifier, patient information, and imaging information received from an imaging sensor, the table configured to be positioned in a bore of the medical imaging device, the selected clinical intent identifier indicating a scan objective, a patient orientation, and/or one or more scan parameters for an imaging scan of a patient with the medical imaging device.

16. The method of claim 15, wherein automatically prepositioning the table according to the imaging information received from the imaging sensor comprises automatically prepositioning the table according to one or more of depth information and visible light information received from the imaging sensor.

17. The method of claim 16, further comprising, after automatically prepositioning the table to a determined position, acquiring medical imaging data with an image source of the medical imaging device responsive to the table reaching the determined position.

18. The method of claim 15, further comprising determining a target table elevation, a reference anatomy, and a target start scan location from the selected clinical intent identifier and adjusting a position of the table according to the target table elevation, the reference anatomy, and the target start scan location and further based on feedback from the imaging information in order to preposition the table.

19. A method for operating a medical imaging device, comprising:
    receiving a selection of an imaging protocol and an associated clinical intent identifier for an imaging scan of a patient with the medical imaging device;
    determining a table elevation, an anatomical reference, and a start scan location for the imaging scan based on output from a look-up table that only uses the clinical intent identifier as an input; and
    adjusting a position of a table to a determined position based on the table elevation, the anatomical reference, and the start scan location, the table configured to be positioned in a bore of the medical imaging device.

20. The method of claim 4, wherein the patient information comprises an x-ray dose threshold for the patient to generate the final table elevation.

* * * * *